US00PP23889P2

(12) United States Plant Patent
Oostveen

(10) Patent No.: US PP23,889 P2
(45) Date of Patent: Sep. 10, 2013

(54) ***HIBISCUS* PLANT NAMED 'EXTREHOTPINK'**

(50) Latin Name: *Hibiscus moscheutos*
Varietal Denomination: Extrehotpink

(75) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 59 days.

(21) Appl. No.: 13/373,740

(22) Filed: Nov. 28, 2011

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — C. A. Whealy

(57) ABSTRACT

A new and distinct cultivar of *Hibiscus* plant named 'Extrehotpink', characterized by its upright and somewhat outwardly spreading plant form; dark green-colored rounded leaves; freely flowering habit; large intense red purple-colored flowers with dark red-colored centers and darker red purple-colored venation; and good flower longevity.

2 Drawing Sheets

Botanical designation: *Hibiscus moscheutos.*
Cultivar denomination: 'EXTREHOTPINK'.

BACKGROUND OF THE INVENTION

The present invention relates to a new and distinct cultivar of *Hibiscus* plant, botanically known as *Hibiscus moscheutos* and hereinafter referred to by the name 'Extrehotpink'.

The new *Hibiscus* plant is a product of a planned breeding program conducted by the Inventor in De Kwakel, The Netherlands. The objective of the breeding program is to create new *Hibiscus* plants with attractive and large flowers.

The new *Hibiscus* plant originated from a cross-pollination in August, 2009 in De Kwakel, The Netherlands of *Hibiscus moscheutos* 'Guido Pink', not patented, as the female, or seed, parent with *Hibiscus moscheutos* 'Extrepink', disclosed in U.S. Plant Pat. No. 23,130, as the male, or pollen, parent. The new *Hibiscus* plant was discovered and selected by the Inventor as a single flowering plant from within the progeny of the stated cross-pollination in a controlled greenhouse environment in De Kwakel, The Netherlands in July, 2010.

Asexual reproduction of the new *Hibiscus* plant by vegetative cuttings in a controlled greenhouse environment in De Kwakel, The Netherlands since September, 2010 has shown that the unique features of this new *Hibiscus* plant are stable and reproduced true to type in successive generations.

SUMMARY OF THE INVENTION

Plants of the new *Hibiscus* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Extrehotpink'. These characteristics in combination distinguish 'Extrehotpink' as a new and distinct *Hibiscus* plant:

1. Upright and somewhat outwardly spreading plant form.
2. Dark green-colored rounded leaves.

3. Freely flowering habit.
4. Large intense red purple-colored flowers with dark red-colored centers and darker red purple-colored venation.
5. Good flower longevity.

Plants of the new *Hibiscus* can be compared to plants of the female parent, 'Guido Pink'. Plants of the new *Hibiscus* differ primarily from plants of 'Guido Pink' in the following characteristics:

1. Plants of the new *Hibiscus* are not as freely branching as plants of 'Guido Pink'.
2. Plants of the new *Hibiscus* have larger flowers than plants of 'Guido Pink'.
3. Plants of the new *Hibiscus* and 'Guido Pink' differ in flower color as plants of 'Guido Pink' have pink-colored flowers.

Plants of the new *Hibiscus* can be compared to plants of the male parent, 'Extrepink'. Plants of the new *Hibiscus* differ primarily from plants of 'Extrepink' in the following characteristics:

1. Leaves of plants of the new *Hibiscus* are darker green in color than leaves of plants of 'Extrepink'.
2. Flower petals of plants of the new *Hibiscus* are more imbricate than flower petals of plants of 'Extrepink'.
3. Plants of the new *Hibiscus* and 'Extrepink' differ in flower color as plants of 'Extrepink' have light red purple-colored flowers.

Plants of the new *Hibiscus* can be compared to plants of *Hibiscus moscheutos* 'Mauvelous', not patented. Plants of the new *Hibiscus* differ primarily from plants of 'Mauvelous' in the following characteristics:

1. Plants of the new *Hibiscus* are more compact than and not as vigorous as plants of 'Mauvelous'.
2. Flower petals of plants of the new *Hibiscus* are more imbricate than flower petals of plants of 'Mauvelous'.
3. Plants of the new *Hibiscus* and 'Mauvelous' differ in flower color as plants of 'Mauvelous' have pink-colored flowers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Extrehotpink' grown in a container.

The photograph at the top of the second sheet is a close-up view of a typical flower of 'Extrehotpink'.

DETAILED BOTANICAL DESCRIPTION

The aforementioned photographs and following observations, measurements and values describe plants grown during the late summer in five-liter containers in a glass-covered greenhouse in De Kwakel, The Netherlands and under cultural practices which closely approximate commercial *Hibiscus* production. During the production of the plants, day temperatures ranged from 18° C. to 33° C. and night temperatures ranged from 18° C. to 25° C. Plants were 14 weeks old when the photographs and the description were taken. In the description, color references are made to The Royal Horticultural Society Colour Chart, 2007 Edition, except where general terms of ordinary dictionary significance are used.

Botanical classification: *Hibiscus moscheutos* 'Extrehotpink'.

Parentage:

*Female, or seed, parent.*—*Hibiscus moscheutos* 'Guido Pink', not patented.

*Male or pollen parent.*—*Hibiscus moscheutos* 'Extrepink', disclosed in U.S. Plant Pat. No. 23,130.

Propagation:

*Type.*—By vegetative cuttings.

*Time to initiate roots, summer.*—About seven days at temperatures of 22° C.

*Time to initiate roots, winter.*—About ten days at temperatures of 19° C.

*Time to produce a rooted young plant, summer.*—About three weeks at temperatures of 21° C.

*Time to produce a rooted young plant, winter.*—About four weeks at temperatures of 18° C.

*Root description.*—Medium in thickness, fibrous; white to light brown in color.

*Rooting habit.*—Freely branching; dense.

Plant description:

*Plant form and growth habit.*—Upright and somewhat outwardly spreading plant form, broad inverted triangular plant form; moderately vigorous growth habit.

*Branching habit.*—Moderate branching habit, usually about ten lateral branches develop; pinching enhances lateral branch development.

*Plant height.*—About 72.5 cm.

*Plant diameter* (*area of spread*).—About 68 cm.

Lateral branch description:

*Length.*—About 53.6 cm.

*Diameter.*—About 5 mm.

*Internode length.*—About 3.7 cm.

*Strength.*—Moderately strong.

*Texture.*—Smooth, glabrous.

*Color.*—Close to 143C.

Foliage description:

*Arrangement.*—Alternate, single.

*Length.*—About 10.2 cm.

*Width.*—About 7.6 cm.

*Shape.*—Ovate.

*Apex.*—Acuminate to apiculate.

*Base.*—Cordate.

*Margin.*—Bluntly crenate to serrate.

*Texture, upper and lower surfaces.*—Smooth, glabrous.

*Venation pattern.*—Pinnate.

*Color.*—Developing leaves, upper surface: Close to N137D. Developing leaves, lower surface: Between 137D and 138B. Fully expanded leaves, upper surface: Darker than between N137D and 147A; venation, close to 144A. Fully expanded leaves, lower surface: Close to 147B; venation, close to 144B.

*Petiole.*—Length: About 7.4 cm. Diameter: About 3 mm. Texture, upper and lower surfaces: Smooth, glabrous. Color, upper and lower surfaces: Close to 144A.

Flower description:

*Flower arrangement.*—Large rotate flowers arranged singly at terminal leaf axils; freely flowering habit with about 50 flowers developing per plant; flowers face mostly outwardly to slightly upright.

*Fragrance.*—None detected.

*Flower longevity.*—Good flower longevity, flowers last for about four days; flowers not persistent.

*Natural flowering season.*—Plants flower from late summer into the autumn in The Netherlands; plants begin flowering about ten weeks after planting.

*Flower diameter.*—About 19.5 cm.

*Flower length* (*height*).—About 6.2 cm.

*Flower bud.*—Rate of opening: Flowers buds open in about four days. Length: About 4.2 cm. Diameter: About 3.2 cm. Shape: Ovate. Color: Close to 143B to 143C; towards the apex, close to 53A.

*Petals.*—Arrangement: Corolla consists of five petals in a single whorl; petals imbricate. Length: About 10.2 cm. Width: About 11.1 cm. Shape: Broadly obovate to nearly orbicular. Apex: Rounded. Base: Attenuate. Margin: Entire. Texture, upper and lower surfaces: Smooth, glabrous; rugose. Color: When opening and fully opened, upper surface: Close to between 64C to N66C; towards the base, close to 53A; venation, close to 61B to 61C; color becoming closer to 64B with development. When opening and fully opened, lower surface: Close to 63A; towards the base, close to 63B.

*Sepals.*—Appearance: Five sepals fused into a tubular star-shaped calyx. Length: About 3.2 cm. Width: About 1.9 cm. Shape: Ovate. Apex: Abruptly acute. Margin: Entire. Texture, upper and lower surfaces: Smooth, glabrous. Color, immature, upper surface: Close to 143C. Color, immature, lower surface: Close to 143B to 143C. Color, mature, upper and lower surfaces: Close to 143C.

*Peduncles.*—Length: About 5.5 cm. Diameter: About 2 mm. Angle: About 20° from the lateral branch axis. Strength: Moderately strong. Texture: Smooth, glabrous. Color: Close to 144A.

*Reproductive organs.*—Androecium: Stamen number: Numerous, about 150. Filament length: About 4 mm. Filament color: Close to 62C and N155C to N155C. Anther shape: Orbicular. Anther length: About 2 mm. Anther color: Close to N199B. Amount of pollen: Abundant. Pollen color: Close to 11A. Gynoecium: Pistil length: About 4 cm. Style length: About 3.8 cm. Style color: Close to 55B to 55D. Stigma appearance:

Five-parted, club-shaped. Stigma color: Close to 53A. Ovary color: Close to 150C.

*Seeds and fruits*.—Seed and fruit development have not been observed on plants of the new *Hibiscus*.

Temperature tolerance: Plants of the new *Hibiscus* have been observed to tolerate high temperatures of about 35° C. and to be hardy to USDA Hardiness Zone 6.

Pathogen & pest resistance: Plants of the new *Hibiscus* have not been observed to be resistant to pathogens and pests common to *Hibiscus*.

It is claimed:

1. A new and distinct *Hibiscus* plant named 'Extrehotpink' as illustrated and described.

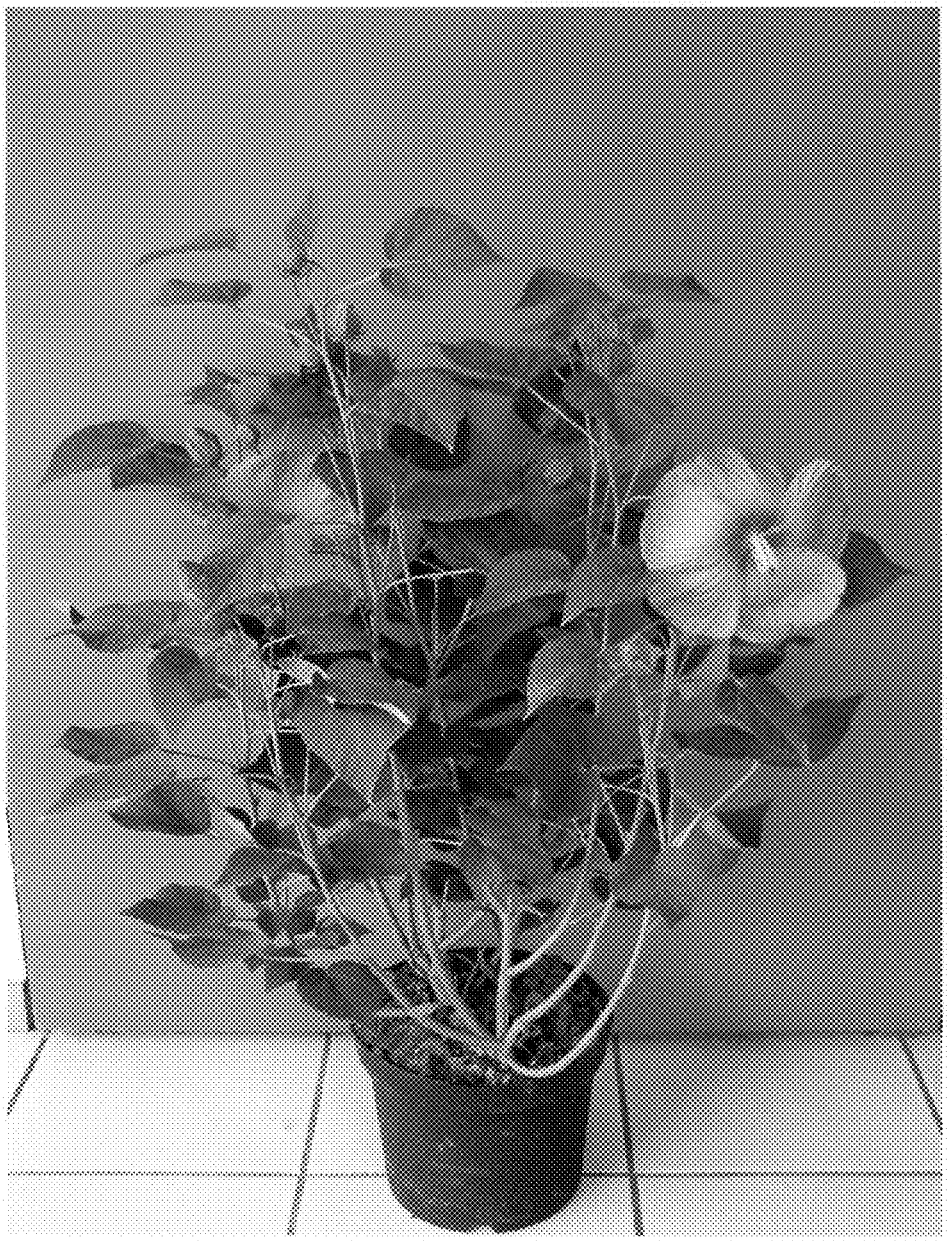

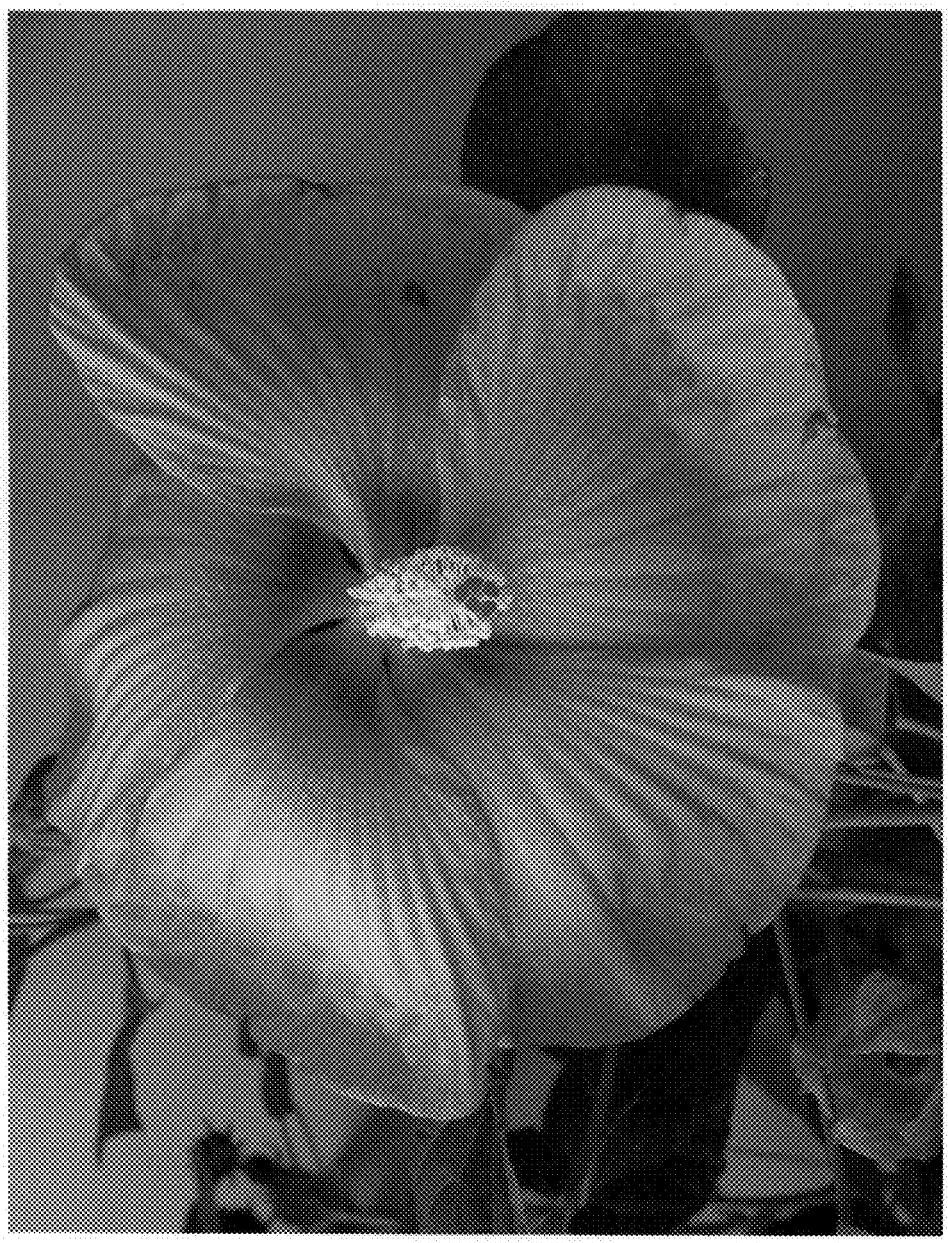

* * * * *